United States Patent [19]

Span et al.

[11] Patent Number: 4,885,998
[45] Date of Patent: Dec. 12, 1989

[54] PATIENT SUPPORT SYSTEM FOR RADIOTHERAPY

[75] Inventors: Francis J. Span; Leopold H. Hissel, both of Eindhoven, Netherlands; Leonardus J. Grassens, Chipita Park, Colo.

[73] Assignee: U.S. Philips Corporation, New York, N.Y.

[21] Appl. No.: 168,354

[22] Filed: Mar. 15, 1988

[30] Foreign Application Priority Data

Mar. 16, 1987 [GB] United Kingdom ................. 8706152

[51] Int. Cl.⁴ ............................................. A47B 11/00
[52] U.S. Cl. ..................................... 108/139; 108/22; 378/209; 269/322
[58] Field of Search ........................ 108/22, 43, 95, 96, 108/139, 141, 144, 148; 5/60; 248/283; 378/208, 209, 210, 195, 198; 269/322, 325

[56] References Cited

U.S. PATENT DOCUMENTS

| | | | |
|---|---|---|---|
| 2,713,437 | 7/1985 | Broden | 108/139 X |
| 2,906,143 | 9/1959 | Musser. | |
| 3,306,134 | 2/1967 | Winiarski. | |
| 3,627,250 | 12/1971 | Pegrum | 378/209 X |
| 3,745,996 | 7/1973 | Rush, Sr. | 378/209 X |
| 3,766,384 | 10/1973 | Anderson | 378/209 |
| 3,963,288 | 6/1976 | Burnett | 108/139 X |
| 4,131,802 | 12/1978 | Braden et al. | 269/322 X |
| 4,345,847 | 8/1982 | Schiff et al. | 403/103 |
| 4,523,070 | 6/1985 | Jorgensen et al. | 108/139 X |

Primary Examiner—Kenneth J. Dorner
Assistant Examiner—Jose V. Chen
Attorney, Agent, or Firm—Thomas A. Briody; Jack E. Haken; Jack D. Slobod

[57] ABSTRACT

A patient support system for irradiation therapy or treatment simulation comprises a main arm 1 on a sub-floor mounted pivot 10 about a first vertical axis 17, which supports a further arm 49 rotatable about a second vertical axis 16. At the other end of the arm 49 a vertical pillar 4, pivotable about a third vertical axis 15, supports a vertically displaceable carriage 3 on which a patient support table top 2 is directly mounted. A control system is described which enables x, y coordinate command values to control respective drives associated with the three vertical axes to position a patient quickly and accurately relative to the treatment isocenter. The system requires only a shallow well while providing a large range of vertical lift. Furthermore, no sub-table x-y carriage is required increasing patient accessibility.

14 Claims, 10 Drawing Sheets $$\alpha \equiv ALPHA \; ; \;\; \beta \equiv BETA \; ; \;\; \emptyset \equiv PHI.$$

$$Xa = X1 + r1 \cdot \cos \emptyset 1 + r2 \cdot \cos(\emptyset 1 + \emptyset 2) + r3 \cdot \cos(\emptyset 1 + \emptyset 2 + \emptyset 3 + \beta) \tag{1}$$

$$Ya = Y1 + r1 \cdot \sin \emptyset 1 + r2 \cdot \sin(\emptyset 1 + \emptyset 2) + r3 \cdot \sin(\emptyset 1 + \emptyset 2 + \emptyset 3 + \beta) \tag{2}$$

$$\alpha = \emptyset 1 + \emptyset 2 + \emptyset 3 \tag{3}$$

$$X(3)a = Xa - X3 = r3 \cdot \cos(\alpha + \beta) \tag{4}$$

$$Y(3)a = Ya - Y3 = r3 \cdot \sin(\alpha + \beta) \tag{5}$$

$$X(1)3 = X3 - X1 = r1 \cdot \cos \emptyset 1 + r2 \cdot \cos(\emptyset 1 + \emptyset 2) \tag{6}$$

$$Y(1)3 = Y3 - Y1 = r1 \cdot \sin \emptyset 1 + r2 \cdot \sin(\emptyset 1 + \emptyset 2) \tag{7}$$

$$Xa = X1 + X(1)3 + X(3)a \tag{8}$$

$$Ya = Y1 + Y(1)3 + Y(3)a \tag{9}$$

$$\frac{\partial X}{\partial \emptyset 1} = -r1 \left[ \sin \emptyset 1 + a \cdot \sin(\emptyset 1 + \emptyset 2) \right] \tag{10}$$

$$\frac{\partial Y}{\partial \emptyset 1} = r1 \left[ \cos \emptyset 1 + a \cdot \cos(\emptyset 1 + \emptyset 2) \right] \tag{11}$$

$$a = \frac{r2}{r1} \tag{12}$$

$$\frac{\partial X}{\partial \emptyset 2} = -r2 \cdot \sin(\emptyset 1 + \emptyset 2) \tag{13}$$

$$\frac{\partial Y}{\partial \emptyset 2} = r2 \cdot \cos(\emptyset 1 + \emptyset 2) \tag{14}$$

$$E\emptyset 1 = EX \cdot \frac{\partial X}{\partial \emptyset 1} + EY \cdot \frac{\partial Y}{\partial \emptyset 1} \tag{15}$$

$$E\emptyset 2 = EX \cdot \frac{\partial X}{\partial \emptyset 2} + EY \cdot \frac{\partial Y}{\partial \emptyset 2} \tag{16}$$

$$E\emptyset 3 = \alpha - (\emptyset 1 + \emptyset 2 + \emptyset 3) \tag{17}$$

PATIENT SUPPORT SYSTEM FOR RADIOTHERAPY

BACKGROUND OF THE INVENTION

The invention relates to a patient support system for irradiation therapy or treatment simulation, comprising a main supporting arm rotationally attached at one end to a structural support by a first support bearing so as to be rotatable about a first vertical axis fixedly located relative to the treatment isocentre, a patient support table top and interconnecting support means connecting the table top to the other end of the main supporting arm so that the table top can be displaced vertically and horizontally relative to the treatment isocentre.

Radiation therapy involves directing a beam of high energy radiation such as hard x-rays or gamma rays from a suitable source, for example an isotope or a high energy x-ray tube using an electron accelerator, suitably a linear accelerator, at a selected region of the body of a patient in which malignant cells are present. A dosage is employed which is lethal to such cells, however, in order to minimise damage to other parts of the body, the dose applied to the surrounding tissue is reduced by rotating the direction of the irradiation beam about a central point called the treatment isocentre, which is located at or near the centre of the selected body region to be irradiated.

For this purpose a source of high energy radiation is mounted in counterbalanced manner on a gantry so as to be capable of rotation about a horizontal axis through the isocentre. The source is heavily screened to reduce generally emitted radiation to a reasonably safe amount and the emergent irradiation beam is limited by a diaphragm which defines the boundaries of the region of the patient to be irradiated, in a manner such that radiation is generally directed radially towards the isocentre. The source and gantry assembly is consequently very massive and is normally fixed to the structure of the associated building. This means that the isocentre is fixed in space within the treatment room. It is therefore a requirement for a patient support system that it should be capable of supporting and displacing a patient in an accurate and reproducible manner so that any body region to be irradiated can be located at the isocentre and positioned relative to the scanning arc of the radiation source so that irradiation may be applied to the patient along selectable directions of incidence.

A presently used form of patient support system of the kind referred to comprises a floor mounted relatively small turntable which is rotatable about a vertical axis usually through the isocentre and supports a radial arm extension the outer end of which is connected to a patient support table top by interconnecting support means in the form of a rotatably mounted pedestal base having an under table lift for vertical displacement and on the top of which is mounted a carriage assembly formed by a tandem arrangement of respective lateral and longitudinal horizontal displacement carriages, the table top being attached to the uppermost carriage. This form of patient support typically employs a form of scissors jack to provide the lift. Because of the relatively short stroke obtainable by such a jack and the need for a low minimum table height of about 70 cm for the convenience of patient access to the table top, this results in a relatively low maximum lifting height of about 120 cms. The maximum lifting height can be raised by the use of an underfloor pit. In some high energy installations the isocentre is even higher and a larger range of height adjustment can be provided using a hydraulic ram lift mounted on a more extensive turntable. This, however, requires the presence of a correspondingly deep underfloor pit to accommodate the ram housing resulting in higher installation costs and may not in some cases be structurally possible.

A further disadvantage of the above described patient support system concerns the carriage assembly for providing the horizontal displacement of the table top in two dimensions since the carriages and associated parallel rails render the assembly bulky and heavy, and tend to restrict access to the patient.

SUMMARY OF THE INVENTION

It is an object of the invention to provide an improved patient support system for irradiation therapy which can reduce these difficulties and which can be simple and convenient to operate in conjunction with computer controlled treatment and simulation equipment.

In accordance with the invention there is provided a patient support system for irradiation therapy or treatment simulation, comprising a main supporting arm rotationally attached at one end to a structural support by a first support bearing so as to be rotatable about a first vertical axis fixedly located relative to the treatment isocentre, a patient support table top and interconnecting support means connecting the table top to the other end of the main supporting arm so that the table top can be displaced vertically and horizontally relative to the treatment isocentre, characterized in that the interconnecting support means comprise a further supporting arm rotationally attached at one end to said other end of the main supporting arm by a second support bearing so as to be rotatable about a second vertical axis, and vertical support means rotationally attached to the other end of the further supporting arm by a third support bearing so as to be rotatable about a third vertical axis, the patient support table top being attached to supporting carrier means, and the vertical support means includes means for locating and vertically displacing the supporting carrier means.

The vertical support means preferably comprises a single vertical supporting pillar of rigid closed box construction, the supporting carrier means preferably comprises a vertically displaceable carriage of rigid box construction and the means for locating and vertically displacing the supporting carrier means preferably include two longitudinal guide tracks which are rigidly mounted adjacent one another with their lateral directions at a mutual angle preferably at right angles, on a supporting surface having a correspondingly angled open V-shaped transverse section, which is rigidly connected to the vertical supporting pillar, the vertically displaceable carriage being provided with bearing members which engage the corresponding longitudinal guide tracks so as to locate and support the carriage in a vertically displaceable manner relative to the pillar. The V-shaped supporting surface can be formed by an outer wall surface of the pillar, and the means for vertically displacing the supporting carrier can comprise a motor driven rotatable screw threaded shaft mounted in a thrust bearing supported by the vertical supporting pillar, said shaft engaging a corresponding nut attached to the vertically displaceable carriage.

The main supporting arm can be located entirely below the floor of a treatment room and an arcuate aperture can be provided in the floor surface to accommodate connecting means connecting said other end of the main supporting arm to one end of the further supporting arm which is situated above the floor via the second support bearing, the arcuate aperture being covered by a flexible cover strip which is passed through a passageway formed in the connecting means. The flexible cover strip can comprise a plurality of adjacent transversely arranged load-bearing strips or segments flexibly linked to one another, and the inner and outer sides of the arcuate aperture are each preferably provided with a supporting ledge arranged so that each segment can be supported at each end by a corresponding ledge with the upper surface of the flexible cover strip flush with the surface of the floor. A smooth-walled duct and/or an arrangement of bearing rollers can be disposed along the path of the flexible strip through the passageway so as to guide the flexible strip past connecting supports forming the connecting means.

Alternatively the main supporting arm can comprise a first arm portion attached to the first support bearing and supporting a turntable surface level with the surface of the floor, and a further arm portion extending outwardly above the floor level from the outer part of the turntable surface, the second support bearing being attached to the outer end of the further arm portion.

Preferably the first, second and third support bearing and the means for vertically displacing the supporting carrier means are each provided with corresponding motor drives suitably employing electric drive motors and associated output shaft angular position and velocity sensing means, control means being provided for controlling the motor drives in response to the outputs of the associated sensing means and to corresponding position demand values resulting from instructions provided by the operator and respective motor drives arranged to provide corresponding angular displacements about the first, second and D third vertical axes can be controlled by computer means. The computer means can comprise one or more microprocessors and the motor drives can employ d.c. electric motors. Preferably electric motor drives associated with the first, second and third support bearings, include reduction gearing employing a harmonic drive, for example a strain wave, gear arrangement.

BRIEF DESCRIPTION OF THE DRAWING

Embodiments of the invent will now be described by way of example, with reference to the accompanying drawings of which:

FIG. 11 is a sheet of equations used in the patient support system.

DETAILED DESCRIPTION OF THE PREFERRED EMBODIMENT

Figure 1:
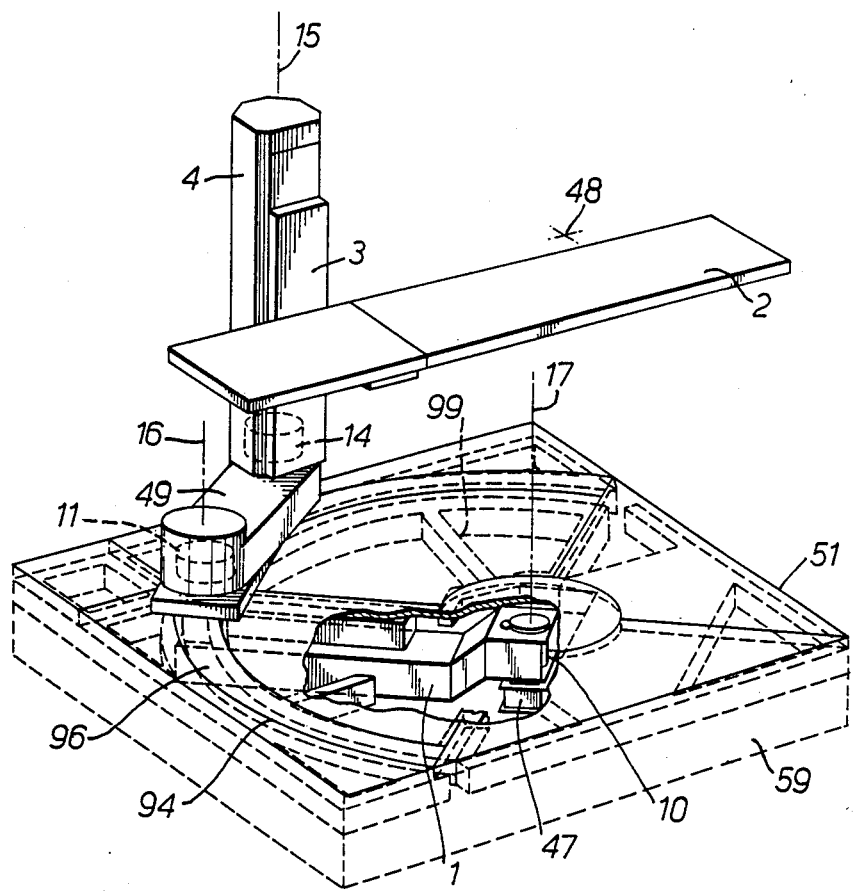
FIG. 1 is a perspective view, partly cut away, illustrating diagrammatically a patient support system in accordance with the invention.

Reference will now be made to FIG. 1 which illustrates a patient support system for irradiation therapy or treatment simulation in accordance with the invention. A main supporting arm 1 is rotationally attached at one end by means of a first support bearing 10, suitably two spaced heavy duty single race ball bearings, to a structural support in the form of an underfloor mounting frame 47 fixed to the substructure of the floor 51 of the treatment room in a shallow well 59, so as to be rotatable about a first vertical axis 17. The axis 17 can, if desired, pass through the treatment isocentre 48 of an associated counterbalanced gantry-mounted high-energy irradiation source (not shown), but will in any event be fixed relative thereto since the irradiation source gantry will also be fixedly attached to the structure of the treatment building. A patient support 2 is connected to the other end of the main supporting arm 1 by interconnecting support means 4, 49 , so that the table top 2 can be displaced vertically and horizontally relative to the treatment isocentre 48.

In accordance with the invention the interconnecting support means comprise a further supporting arm 49 rotationally attached at one end to the unsupported end of the main supporting arm 1 by means of a second support bearing 11, suitably in the form of two spaced single race ball bearings, so as to be rotatable about a second vertical axis 16, and vertical support means in the form of a single vertical supporting pillar 4 rotationally attached to the other end of the further supporting arm 49 by a third support bearing 14, suitably in the form of two spaced single race ball bearings, so as to be rotatable about a third vertical axis 15. The patient support table top 2 is attached to supporting carrier means in the form of a vertically displaceable carriage 3, and the pillar 4 includes means for locating and vertically displacing the carriage 3 as will now be described with reference to FIGS. 2, 3 and 4.

Figure 2:
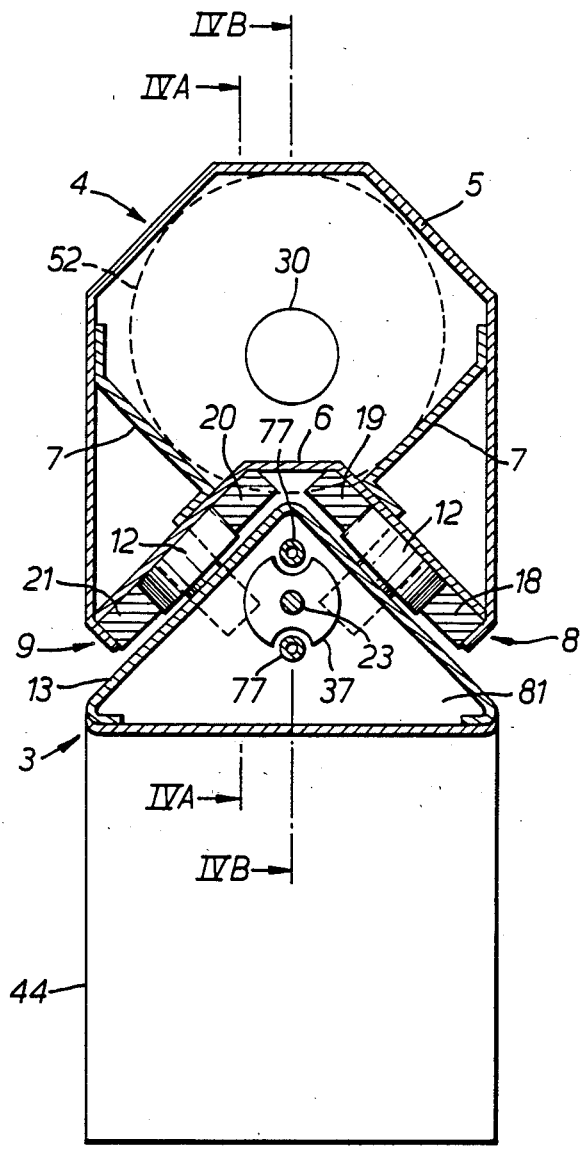
FIG. 2 is a cross section of a vertical supporting pillar employed in FIG. 1.
Figure 3:
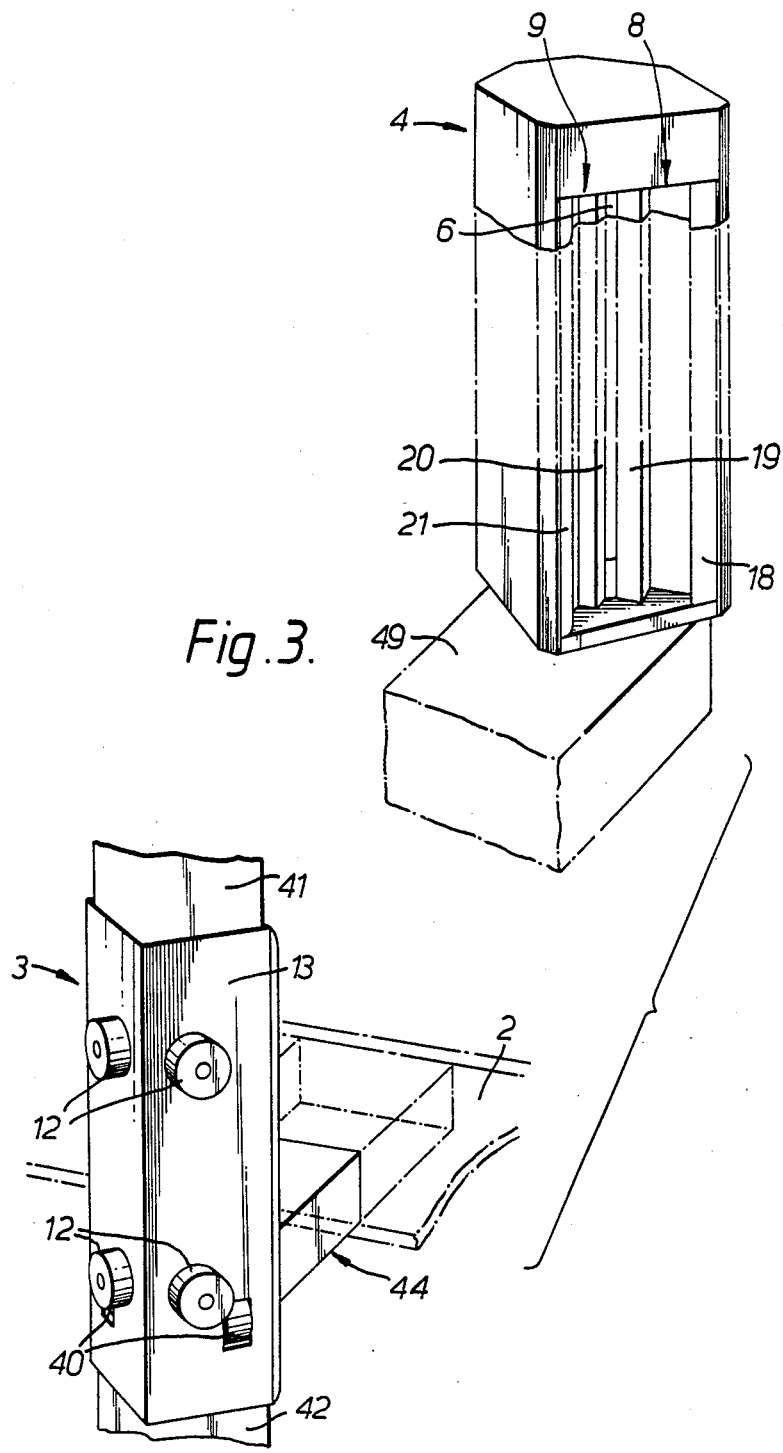
FIG. 3 is a disassembled perspective diagram illustrating the parts of FIG. 2.

FIG. 2 is a horizontal cross-section through the pillar 4 and the carriage 3 and illustrates one form of vertically displaceable coupling therebetween. The pillar 4 is formed as a rigid closed box construction, suitably of shaped panels of sheet steel hole welded together at intervals, so that side walls 5, 6 and 7 form at least one box region having a closed cross-section at substantially all locations along the length of the pillar 4, and a transverse stiffening member, e.g. a top plate 34 or outer bearing sleeve 52, (FIG. 4) hole welded at each end, and if desired, also at intermediate positions, e.g. a bulkhead plate 43, for additional rigidity. The vertically displaceable carriage 3 is of rigid box construction being formed of a V-shaped wall 13 adjacent the pillar 4 stiffened by transverse plates hole welded at intervals along its length. Further stiffening is provided by the table top connection socket 44 hole welded across the open side. The open side of the carriage is closed by a front plate 46 which can be removable for access to the interior, to form a closed box structure of further improved torsional rigidity.

In order to locate the carriage 3 horizontally, the pillar 4 is provided with guide means formed by two longitudinal guide tracks 8 and 9 which are rigidly mounted adjacent one another with their lateral directions at a mutual angle, preferably at right angles, on a supporting surface having a correspondingly angled open V-shaped transverse section and which is rigidly connected to the pillar 4, and in the present example comprises the outer wall surface 6 of the pillar 4. In the present example the guide tracks 8, 9 comprise respective linear recesses each formed between a pair of facing bearing surfaces forming the corresponding sides of respective parallel pairs of steel stripes 18, 19 and 20, 21 of rectangular section firmly fixed to the wall 6. The carriage 3 is provided with bearing members in the form of rollers 12 on the outer side of the wall surface 13. In operation, the rollers 12 are situated in the guide recesses so as to engage the respective pairs of facing side faces of the strips 18, 19 and 20, 21, thus locating and horizontally supporting the carriage 3 in a vertically displaceable manner relative to the pillar 4. Further horizontal support is provided by rollers 40, shown in the disassembled perspective diagram of the cooperating sides of the pillar 4 and the carriage 3 in FIG. 3, which bear, in operation, on the outer surfaces of the respective outer strips 18, 21, and are arranged to prevent frictional contact between that face of the wall surface 13 or the end face of the corresponding rollers 12, and the surface of the strips 18, 19 or 20, 21 and of the wall 6 and also to ensure that the table top 2 is restrained from swinging about a vertical axis passing through the pillar 4.

Figure 4:
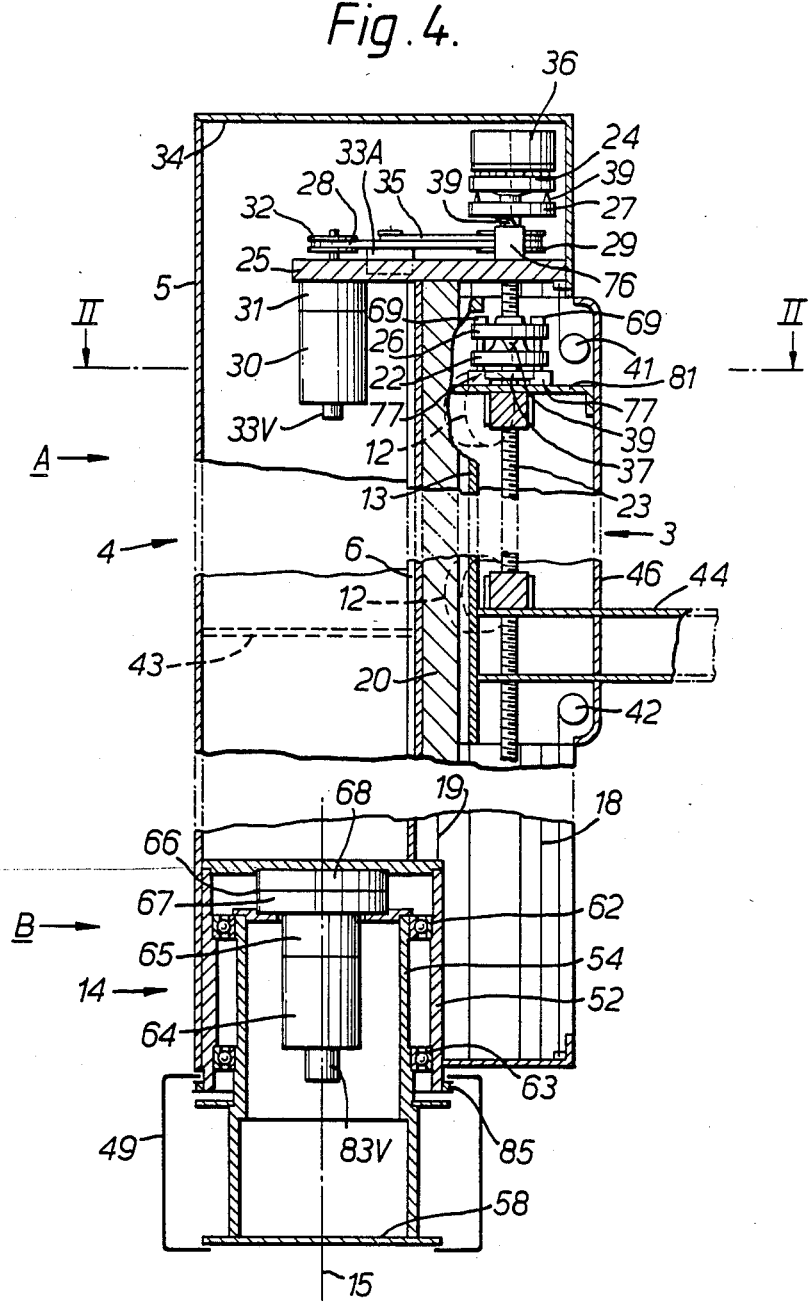
FIG. 4 is a longitudinal section, partly cut away of the vertical support pillar of FIG. 1.

FIG. 4 is a vertical section partly cut away, illustrating the means for vertically displacing the supporting carrier. The carriage 3 is supported and displaced in a vertical direction by means of a motor driven rotatable screw threaded shaft 23 mounted in a thrust bearing 24 supported by a supporting plate 25 forming the upper bulkhead of the box pillar 4, the shaft 23 engaging a corresponding nut 22 attached to the carriage 3. The threaded shaft 23 is driven via a toothed belt 28 which engages a toothed pinion 29 mounted on the shaft 23, and a further toothed pinion 32 on the output shaft of the reduction gear train 31 of a drive motor assembly, suitably employing an electrical drive motor 30. Rotation of the shaft 23 and hence the height of the table top 2, is sensed by an angular position sensor 33A driven by a further toothed belt 35 which also engages the toothed pinion 29 on the shaft 23 and an angular velocity sensor 33V mounted on the shaft of the electrical drive motor 30. A fail-safe brake 36 is fixed to the end of the shaft 23 to hold the vertical table position steady and an idler safety nut 37 is arranged under the nut 22 to operate normally under no-load conditions to act as a safety stop if the thread of the support nut 22 should fail or when a low friction recirculating ball arrangement is used, if the ball cage should burst.

In order to allow for variations in alignment between the supports of the nut 22, the thrust bearing 24 and the threaded shaft 23 as the carriage 3 is displaced vertically on the pillar 4, the nut 22 and the thrust bearing 24 are respectively attached to the carriage 3 and to the supporting plate 25, by a cardanic assembly formed by intermediate suspension plates 26 and 27, respectively. Two pillars 76 located on the supporting plate 25, are diametrically spaced about the axis of the shaft 23 to support the upper intermediate plate 27 via associated bearing projections 39 so that it can tilt about a corresponding diametric transverse axis through the projections 39. The thrust bearing 24 is connected to the upper intermediate plate 27 by two bearing projections 39 which are diametrically spaced about the axis of the shaft 23 in a further transverse direction at right angles to the first mentioned diametric transverse axis so that the thrust bearing 24 is thereby enabled to tilt both about a transverse axis directed along the further transverse direction and about the first mentioned transverse axis. Two pillars 77 located on a transverse plate 81 forming part of the carriage 3, are diametrically spaced about the axis of the shaft 23 and support the lower intermediate support plate 26 by means of corresponding relatively small bolts 69 so that the assembly including the plate 26 can flex slightly and therefore tilt about a corresponding diametric transverse axis through the points of attachment. A flange on the nut 22 is connected to the plate 26 by two bearing projections 39 similarly diametrically spaced about the shaft 23 in a transverse direction at right angles to that of the bolts 69 to enable the nut to tilt about either transverse direction relative to the carriage 3.

In order to protect and to hide the guide tracks 8, 9 and the threaded shaft 23, a respective roller blind 41, 42 is fitted to the upper and lower surfaces of the carriage 3 to extend to the top and bottom of the pillar 4, respectively. The patient support table top 2 is attached to the carriage 3 by means of a connecting bracket 44 which is provided with a releasable table connection means so that different table tops may be substituted e.g. for radiotherapy and for treatment simulation.

The carriage 3 is supported so as to prevent a turning displacement about a horizontal axis due to the loading caused by the table top 2 and the additional weight of a supported patient, by the presence of two rollers 12 spaced apart in the vertical direction in each of the guide tracks 8, 9. In the arrangement shown in FIG. 1, the resultant centre of gravity of the patient and the table top 2 will lie to the right of the pillar 4. Thus in the right hand track 8 the upper- roller 12 will bear against the front strip 8 and the lower roller will bear against the inner strip 9. The resultant centre of gravity will also usually lie to the right of the normal to the centre of the left hand track 9 and consequently the upper roller 12 in that track will bear against the inner strip 20 and the lower roller will bear against the outer strip 21. Clearly the diameters of the rollers 12 must be slightly less than the spacing between the facing surfaces of the corresponding pair of strips 18, 19, or 20, 21, otherwise a roller will contact both faces at once producing frictional resistance to and may even jam any vertical displacement. In a modified arrangement, each roller 12 is replaced by a pair of adjacent rollers each of whose diameter is less than the spacing between the facing surfaces of the guide. To reduce free movement in the coupling, that roller of each pair which does not bear the load torque due to the table and patient, is mounted on a prestressed spring mounting which urges the roller into contact with the adjacent guide surface while the load bearing roller is journalled on a shaft which is rigidly fixed to the carriage 3. In this way a predetermined negative loading torque would need to be applied to the carriage 3 before any free play could occur.

This and other forms of vertical supporting pillar are described in our copending U.K. Patent Application No. 8630411 corresponding to U.S. application Ser. No. 133,583 filed Dec. 16, 1987, and the contents thereof are to be regarded as disclosing suitable forms of and alternatives to the pillar 4 herein described, with respect to the present patient support.

The lower end of the pillar 4 is rigidly attached to the outer cylindrical member 52 of the third support bearing 14, suitably by hole welding. The cylindrical member 52 thus forms the transverse stiffening member for the lower end of the pillar 4. The inner cylindrical member 54 of the third support bearing 14, is rigidly fixed, suitably by hole welding, to the load bearing beam 58 of the further support arm 49. The cylindrical bearing members 52 and 54 are coaxial and are rotatably connected via two spaced ball-races 62, 63.

Rotation of the pillar 4 relative to the further supporting arm 49, about the third vertical axis 15, is effected by means of a motor drive suitably comprising an electric motor 64 with reduction gear box 65 driving a harmonic drive 66 connected between the inner and outer cylindrical bearing members 52 and 54.

One form of harmonic drive is described in U.S. Pat. No. 2,906,143 which discloses various examples of strain wave gearing. In one example, an elliptical strain inducing element having an eccentricity e only slightly different from unity, is centrally mounted on an input shaft driven by, for example, a motor, and is disposed in sliding contact with, or via a ball race to reduce friction, a surrounding elastically deformable first annular toothed member with outwardly facing teeth, attached to one side of the output drive. A rigid second annular toothed member with inwardly facing teeth, is attached to the other side of the output drive which is rotatable relative to the first side thereof, and surrounds the first member at a radial distance such that the outwardly facing teeth on the first member are strained outwardly by the elliptical element within two diametrically opposed angular regions, into contact with the inwardly facing teeth of the second member. The respective numbers of teeth on the two annular members are made slightly different, for example 198 and 200 on the inner and outer members, respectively. Thus in this example, each revolution of the input shaft will displace one side of the output drive relative to the other side thereof by 1/100th of a revolution giving a reduction ratio of 100:1 but greater reductions can be provided by employing a larger number of teeth on each member while maintaining the same difference in the numbers of teeth.

The harmonic drive 66 shown in FIG. 4, preferably employs a form of the strain wave gearing arrangement briefly described above. The drive housing is thus constructed in two parts 67, 68, which are rotatable relative to one another about a vertical axis, namely the third vertical axis 15. One part 67 is secured to the inner cylindrical member 54 of the third support bearing 14 and to one of the annular members so as to form one side of the output drive of the strain wave gear. The other part 68 is secured to the outer cylindrical member 52 of the bearing 14 and to the other annular member of the drive so as to form the other side of the output drive. It does not matter which annular member is connected to which part 67, 68 of the housing. The output from the motor 64 and the gearbox 65 drives the input shaft and hence the strain inducing element of the harmonic drive. The housing of the motor 64 and the gearbox 65 is connected to the part 67 for convenience, but could equally well be connected to the other part 68 if desired.

Many advantages relating to the strain wave gearing arrangement are listed in the US patent but particularly relevant to the present application is that the output torque applied between the two sides 67, 68, of the output drive, i.e. between bearing members 54 and 52, is evenly and progressively distributed over a large proportion of the teeth on the two annular members of which over 50 percent can be in contact at all times. Furthermore this means that the effects of slight errors in tooth formation are averaged out thus providing a high degree of accuracy in the output angle when referred to the rotation of the input shaft of the drive, and it also makes it possible to achieve freedom from backlash.

Other forms of harmonic drive can be employed for the drive 66. The aforementioned US Patent also illustrates a three lobed strain inducer which has self-centring properties relative to the two sides of the output drive. However, it is made clear that the stresses present in a three lobed inducer gear are much greater than in a gear employing the two lobed (elliptical) inducer hereinbefore described for the same output loading, and the three lobed arrangement is therefore less suited to the present application. More traditional forms of harmonic drive include that employing a rigid first annular member mounted on an eccentric circular cam driven by the input shaft, and frequently employed in cyclometer mechanisms inter alia, or one of the various forms of wobble gear mechanisms some of which use bevel gears rather than cylindrical arrangements. These latter forms, however, suffer the disadvantages that the output drive is in general unbalanced about the central axis, that the load will be distributed less evenly over a smaller proportion of the teeth, and that they are prone to backlash since both meshed members are rigid. The preferred strain wave gearing arrangement using an D elliptic strain inducer on the other hand provides a diametrically balanced drive torque between the two elements of the output drive.

The relative angular displacement of the pillar 4 about the third vertical axis 15 relative to the further supporting arm 49 is sensed by an angular position sensor 83A which is mounted on the further supporting arm 49 and is driven via a toothed belt 85 the ends of which are attached to a point on a circumferential region at the lower end of the outer cylindrical member 52 of the third support bearing 14. An angular velocity sensor 83V is conveniently included on the shaft of the drive motor 64.

Figure 5:
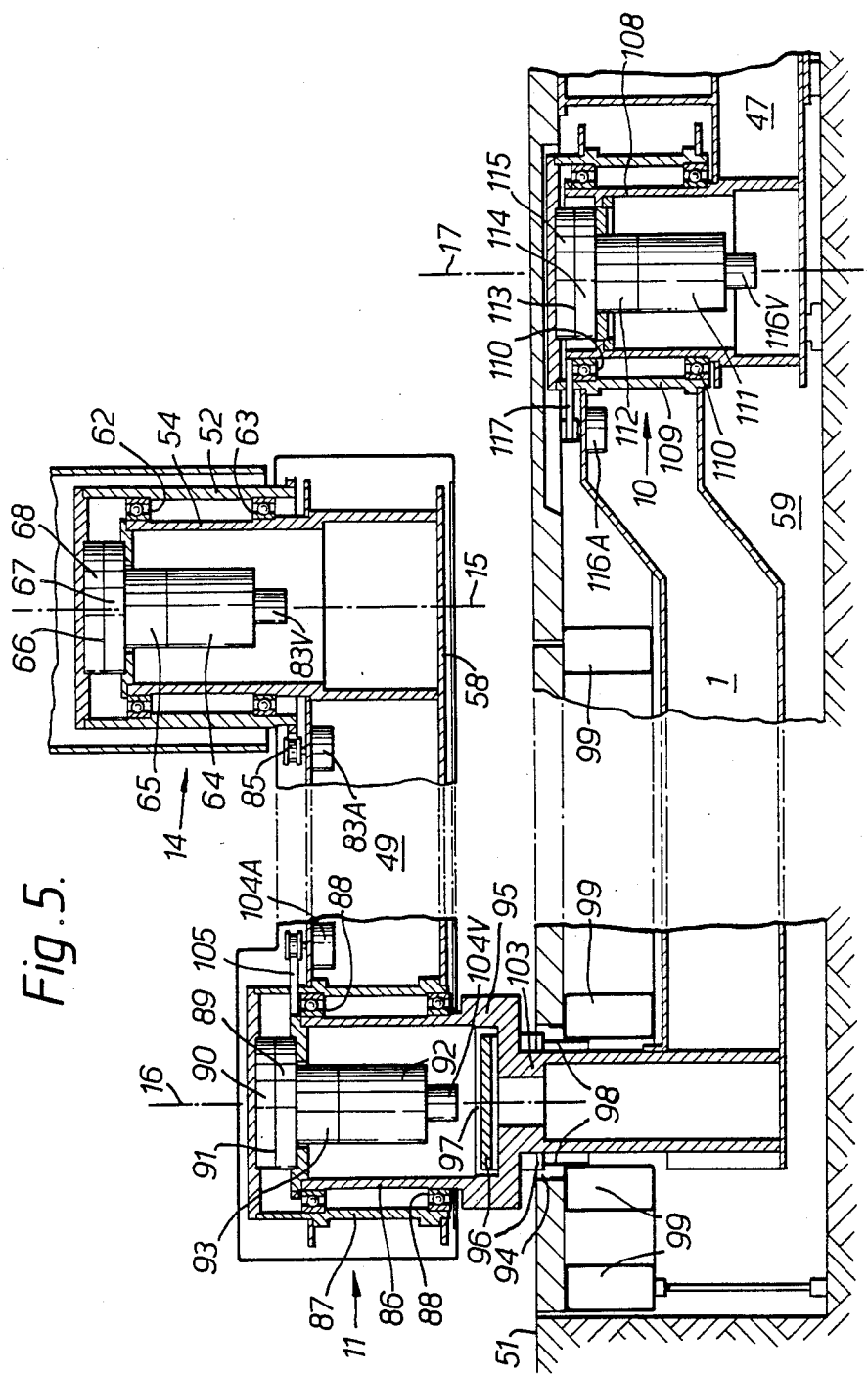
FIG. 5 is a diagrammatic vertical section illustrating part of the supporting arm assembly of FIG. 1.

Referring to FIG. 5, the second support bearing 11 which connects the unsupported end of the main supporting arm 1 to that end of the further supporting arm 49 which is distant from the pillar 4, is basically similar in construction to that of the third support bearing 14. Thus the bearing comprises inner and outer coaxial cylindrical bearing members 86, 87, connected by a spaced pair of ball-races 88 for relative angular displacement about the second vertical axis 16, and rigidly connected to respective output drive parts 89, 90, of a harmonic drive gearbox 91, preferably formed as in the case of the drive 66 by a diametrically induced strain wave gearing arrangement, which together with a motor, suitably an electric drive motor 92 provided with an angular velocity sensor 104V and a reduction gearbox 93 form a motor drive for angularly displacing the arm 49 relative to the main arm 1 about the second vertical axis 16. The load bearing beam 58 of the arm 49 is rigidly attached, suitably by hole welding, to the outer bearing member 87.

The relative angle between the arms 1 and 49 is sensed by a sensor 104A mounted on the beam 58 and driven via a toothed belt 105 from the upper rim of the inner bearing member 86 via a slot in the outer bearing member 87.

The main supporting arm 1 is located below the surface of the floor 51 of the treatment room and an arcuate aperture 94 is provided in the floor surface to accommodate connecting means in the form of a supporting extension 95 to the inner bearing member 86, which is rigidly attached to the main supporting arm 1 suitably by hole welding. The arcuate aperture 94 in the floor 51 is covered by a flexible cover strip 96 which is passed through a passageway 97 through the supporting extension 95.

The flexible strip 96 is generally arcuate in plan view as can be seen from FIG. 1, and in order to provide a secure surface for standing on, the strip 96 comprises a plurality of transversely arranged load-bearing segments, virtually strips, 100, flexibly linked to one another, and the inner and outer sides of the arcuate aperture 94 are each provided with a supporting ledge 98 fixedly attached to a floor-supporting frame 99, and arranged so that each segment 100 resting thereon is supported at each end by a corresponding ledge 98 with the upper surface of the flexible cover strip 96 flush with the surface 51 of the floor. The segments 100 can be made of any suitable load-bearing material having sufficient resistance to wear, for example hardwood or metal such as duralumin or steel, suitably pressed from sheet material, or can be a form of high strength high impact resistance plastic formed by injection moulding. The strips can be flexibly linked by a continuous band attached by a suitable adhesive either to the bottom or, preferably, to the top surface of the segments 100. The band may be of plastic reinforced by high tensile flexible filaments or of a suitable woven fabric preferably with a coated exposed surface. An alternative form of construction is to link each segment 100 to its neighbour by means of a hinge whose pivotal axis is directed radially from the first vertical axis 17, to form a hinged track. In this case the upper surface of each segment 100 can be formed as a non-slip flooring surface, or a suitable covering band applied with adhesive provided the effective pivotal axis of the hinge is sufficiently close to the upper surface.

The passageway 97 formed in the supporting extension 95 preferably includes a smooth walled duct 102 to guide the flexible strip 96 past the supporting connecting portions 103 of the supporting extension 95, which must join with sufficient strength the lower part of the extension 95 which is attached to the main supporting arm 1 and is accommodated in the arcuate slot 94, to the inner bearing member 86 so that the further arm 49, the pillar 4, the table top 2 and the patient, when present, are securely supported thereby. As an alternative or in combination with the duct 102, bearing rollers 106, indicated by dashed outlines, are arranged in pairs, with one roller on each side of the centre of the strip 96, at intervals along the path of the flexible strip 96 through the passageway 97 for guidance purposes. Some or all of the rollers 106 may, if desired, be actively driven by electric motors, preferably in response to an angular displacement of the main arm 1 about the first vertical axis 17, to assist the passage of the vertically displaced portion of the strip 96 past the supporting extension 95.

The first support bearing 10 which supports the main arm 1, is of similar construction to that of the second and third support bearings 11, 14, although it must have a slightly heavier loading capacity than the others. The bearing 10 comprises inner and outer coaxial cylindrical bearing members 108, 109, connected by a spaced pair of heavy duty single race ball bearings 110 for the angular displacement of the main arm 1 about the first vertical axis 17. The inner bearing member 108 is rigidly fixed to the underfloor mounting frame 47 which is itself attached to the substructure of the floor 51 in the well 59. The outer bearing member 109 is fixedly attached to the arm 1, suitably by hole welding. Rotary displacement of the arm 1 about the axis 17 is effected by means of a motor drive suitably comprising an electric motor 111 provided with a velocity sensor 116V, a reduction gearbox 112 and a harmonic drive gearbox 113. The harmonic drive preferably comprises a strain wave gearing arrangement using a symmetrical two lobed (elliptical) strain inducer as hereinbefore described and the respective output drive parts 114, 115 thereof are rigidly connected to the inner and outer cylindrical bearing members 108, 109, respectively. The angular displacement of the arm 1 about the first vertical axis 17, is sensed by a sensor 116A mounted on the main arm 1 and driven via a toothed belt 117 attached at both ends to respective points on an upper rim of the inner bearing member 108 via a slot-like aperture in the outer bearing member 109. Because of the stresses involved, the surface of the teeth in the harmonic drive must be suitably hardened without adversely affecting the flexibility of the inner annular output drive component.

Figure 6:
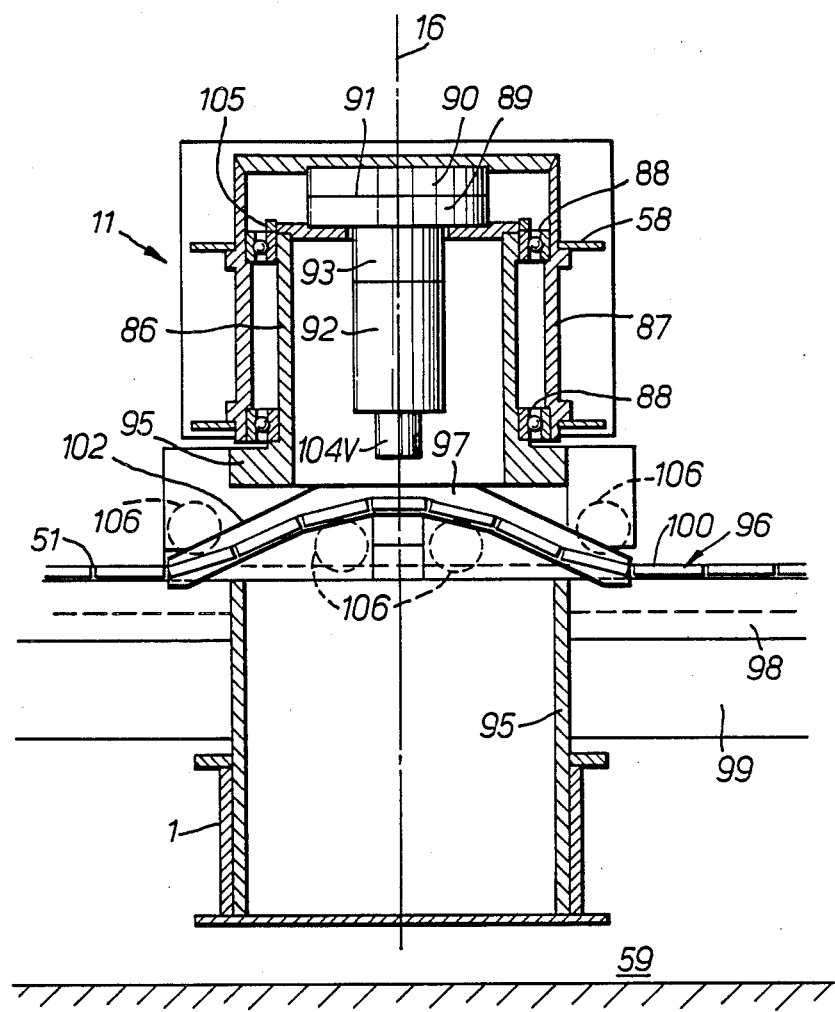
FIG. 6 is a diagrammatic vertical section of a connecting bearing taken at right angles to FIG. 5.

The patient support system illustrated in FIGS. 1, 5 and 6, requires a fairly extensive under-floor well 59 to accommodate SD the main supporting arm 1, and also some form of displaceable cover for the arcuate aperture 94 which is necessary to allow the supporting extension 95 to pass from the supporting end of the main arm 1 below floor level so as to support the bearing 11, the arm 49 and the pillar 4 which are all situated above the floor. Furthermore an extensive supporting framework 99 has to be provided to support a floor surface over the well 59 on either side of the arcuate aperture 94. If it is not possible for structural or economic reasons to provide a well of sufficient size, a modified form of patient support system may be provided in accordance with the invention and as illustrated diagrammatically in FIG. 7, in which the main supporting arm 1 comprises a first arm portion 120 which is fixedly attached, suitably by hole welding, to the outer cylindrical bearing member 109 of the first support bearing 10, and is situated below the floor surface 51, and a further arm portion 121 extending above the floor surface 51. The first arm portion 120, the first support bearing 10 and a mounting frame 127 to which the inner cylindrical bearing member 108 is fixedly attached, suitably by hole welding, are all accommodated in a relatively compact cylindrical well 129, and the first arm portion and the top of the outer bearing member 109 are attached to and support a turntable 122 which forms a covering and supporting floor surface over the well 129. The further arm portion 121 extends outwardly above the floor level from the outer part of the turntable surface and can be formed as an integral extension of the first arm portion 120. The outer end of the further arm portion 121 is rigidly attached to the inner cylindrical bearing member 86 of the second support bearing 11 and is arranged so that the arms 1 and 49 are located close together in a vertical direction. The remainder of this patient support system can be identical to that described with reference to FIGS. 1 to 6. The arrangement of FIG. 7 has the advantage that it requires less structural alteration and is less expensive to install, but has the disadvantage that the central part of the floor surface, namely the turntable 122 will turn with the main arm 1 and the further arm portion 121 above the floor will form a mobile obstruction within the working area around the patient support table top.

Figure 7:
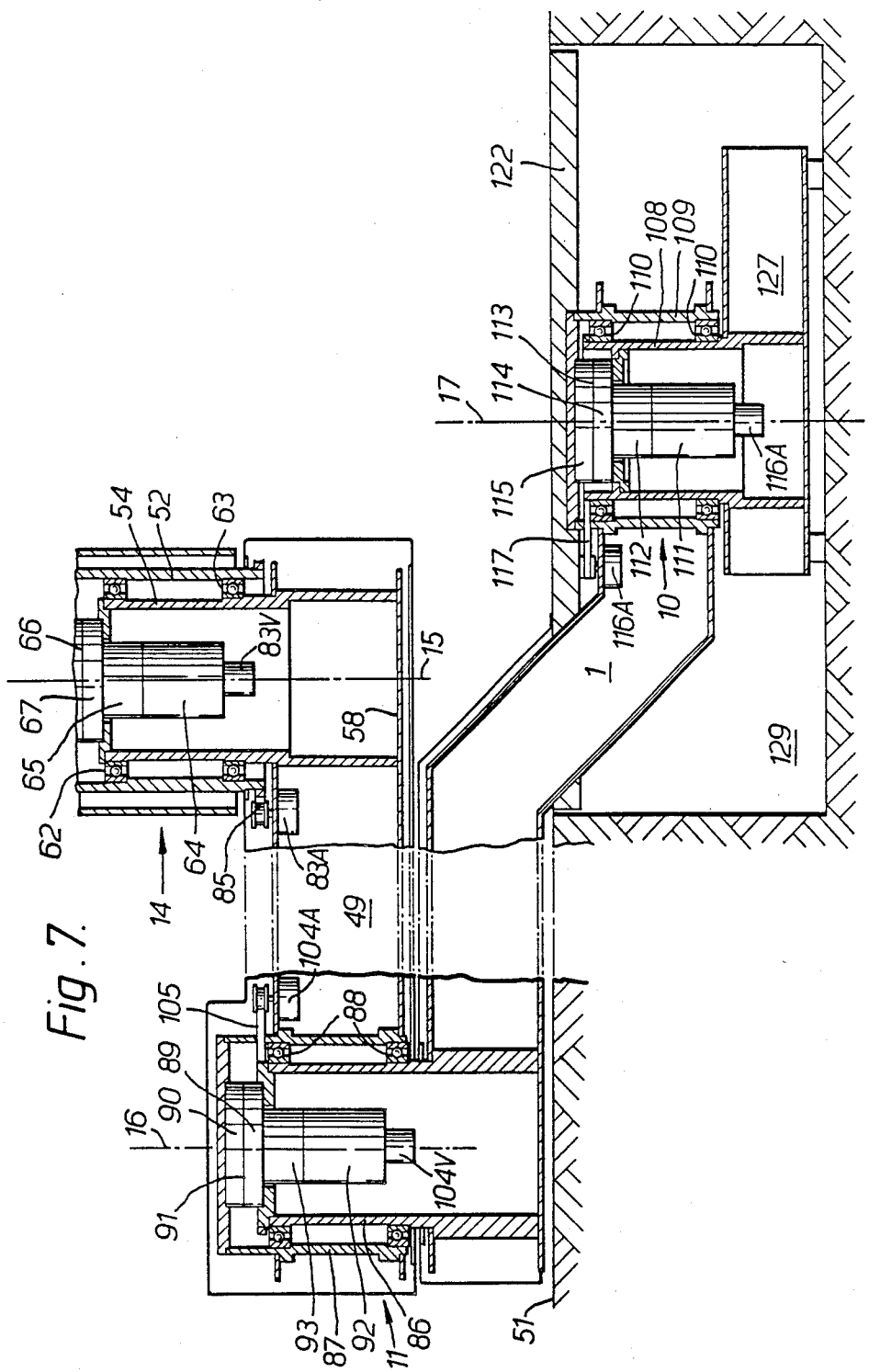
FIG. 7 is a diagrammatic vertical section illustrating part of the supporting arm assembly of a modified patient support system in accordance with the invention.

In both embodiments it would be usual to provide touch sensitive switching members especially at floor level for operating an electrical cut out for the drive motors should a collision occur with the operator or other obstruction during displacement, and such collisions would be expected to be more frequent in the arrangement of FIG. 7.

The relative lengths of the main and further supporting arms 1 and 49 are preferably chosen so that the longitudinal stroke which the further supporting arm 49 is required to perform to locate any point along the table top and hence in a patient, at the treatment isocentre for the operational range of values for the angle alpha of say $-70$ degrees to $+70$ degrees, can be achieved with a reasonable angular displacement of about 90 degrees about the second vertical axis 16. The length of the main supporting arm 1 in combination with the length of the further arm 49, is preferably arranged so that the pillar 4 can be readily maintained just clear of the region which is swept by the head of the high energy radiation source, usually a linear accelerator, or of the simulation radiographic head and image section, during a normal irradiation treatment or simulation.

Suitable forms of control arrangement will now be considered which enable the treatment region of a patient supported by the support table top 2 to be readily positioned in the treatment zone about the isocentre in response to an operator command or a suitable stored treatment program.

Each of the motor drives which in the present example are assumed to be actuated by electric drive motors, can be arranged as a form of set-point servo in which a set-point input value representing a vertical position Z in the case of the motor drive 30, 31, or a relative angular displacement in the case of the drives for the support bearings 10, 11 and 14, is compared in a comparator or by some other process of subtraction, with an actual value measured by an associated sensor, to provide an error signal to drive the corresponding motor in a direction which will reduce the error. The usual servo techniques of velocity feedback for damping oscillations and of integration and feed-forward for reducing steady state errors, can be employed as and where necessary to increase accuracy. A patient support system in accordance with the invention, is preferably provided with coordinated control means which can suitably include a computer or one or more microprocessors, to control the electric motor drives which provide the angular displacements about the first, second and third vertical axes 17, 16 and 15, and the vertical displacement of the carriage 3 in response to the associated position sensing means 116A, 104A, 83A and 33A, and to set-point demand values corresponding to demand position commands which the operator can provide directly as an instruction, for example via a keypad, or which can be generated by computer means for example from a therapy treatment program.

Figure 8:
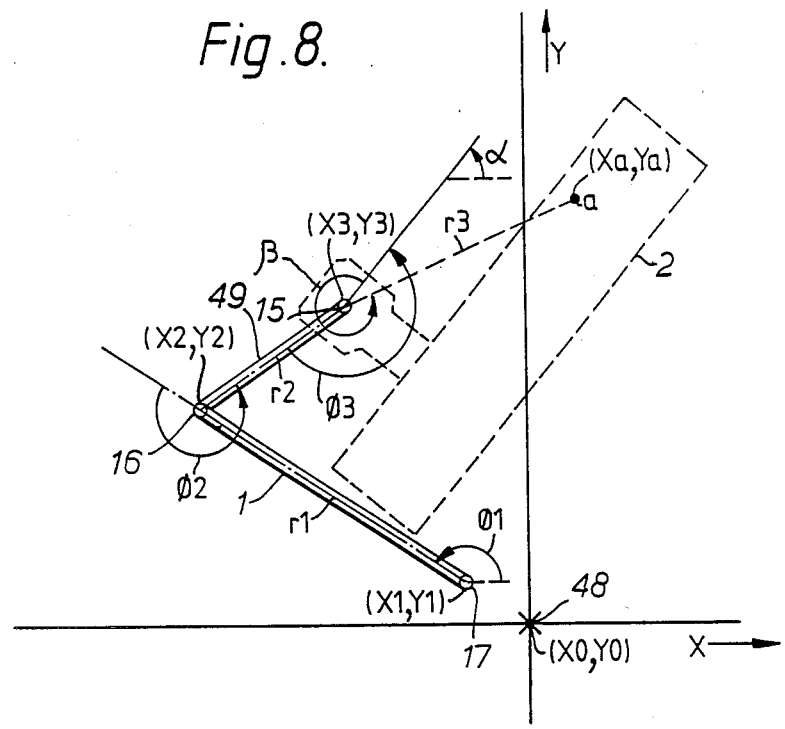
FIG. 8 is a diagram illustrating geometrically the control parameters.

FIG. 8 is a diagram which illustrates the relationship between the components of the patient support system of FIG. 1 and those geometrical parameters relating to a horizontal plane which are employed for the control of the relevant motor drives and for defining a dynamic treatment program relative to the isocentre. It is usual in irradiation therapy to define the patient position in a cartesian coordinate system with the origin X0, Y0, Z0, at the isocentre of the high-energy source gantry.

It is also usual to define an angle alpha as the angle between the longitudinal axis of the patient support table top 2 and the rotation axis of the gantry which latter is also directed along the X-axis. The Z-axis is the vertical axis. The patient position is taken as a specified point, usually at or near the centre of a region in the patient which is to receive treatment, an is indicated by the reference point a in FIG. 8.

The horizontal coordinates of the first vertical axis 17 are X1, Y1, and can if desired, lie at the origin X0, Y0 although this is not essential since a constant offset of (X1−X0), (Y1−Y0), can be simply applied to any calculations in the X-Y plane. The angular position phi1 of the main supporting arm 1 is measured anticlockwise from the X-axis and the second vertical axis 16 is spaced a distance r1 from the first. The angular position phi2 of the further supporting arm 49 is measured anticlockwise from an in-line position relative to the main arm 1. The third vertical axis 15 is spaced a distance r2 from the second axis 16, and the angular position phi3 of the longitudinal axis of the table top is measured from a direction parallel to the arm 49 in an anticlockwise direction as indicated. The coordinate positions of the second and third vertical axes in the X-Y plane are identified as X2, Y2, and X3, Y3, respectively, and will vary with the horizontal adjustment of the table top relative to the first vertical axis X1, Y1 which is permanently fixed.

The reference point a in the treatment region of a patient located on the table top 2, is a horizontal radial distance r3 from the third vertical axis 15 at the point X3, Y3, and the connecting line r3 is inclined at an angle beta measured in an anticlockwise direction about the third vertical axis 15 from the direction of the longitudinal axis of the table top. It should be noted that while r1 and r2 are fixed quantities determined by the apparatus, the values of r3 and beta will vary in an arbitrary manner from one treatment to another and must be determined by the system each time a patient is placed on the table top 2. This can be carried out by manually controlling the support system until the point a, indicated in practice by a visible mark applied to the upper surface of the patient, coincides with the origin X0, Y0 as indicated optically by a light beam projector (not shown) in the high-energy treatment head which latter is orientated on the gantry (not shown) to project the light beam vertically. In this position of the patient, the X and Y coordinates of the point X3, Y3 representing the third vertical axis 15, are determined from the measured values of the angular positions phi1 and phi2 provided by the angular position sensors 116A and 104A, the known constant values of r1 and r2, and the fixed offset between the origin X0 and Y0 and the coordinates X1, Y1 of the first vertical axis 17. From the geometry of the arrangement and the operational requirement that the table axis must be inclined by a preset angle alpha which can be zero, to the x-axis, the angle phi3 must be maintained, e.g. by set-point servo control, so that the sum of
    phi1, phi2 and phi3 always equals alpha (+360 degrees). From this data it is a simple process to compute the values of the distance r3 and the angle beta for example using equations 4 and 5 on the accompanying sheet of equations, and to store the values for use during the course of the subsequent treatment of simulation. In a similar manner, the vertical origin Z0 is determined by reorienting the gantry so that the high-energy source head projects the light beam horizontally and the vertical drive motor 30 is energised so as to make a further optical mark applied to the side of the patient coincide with the projected reference beam. The value which is then read out from the position sensor 33A, is stored as the position of th origin Z0 for the subsequent treatment or simulation.

The coordinated control of the patient support system in accordance with the invention is preferably arranged so that the respective electric motor drives employing the motors 111, 92 and 64 which provide corresponding angular displacements about the first, second and third vertical axes 17, 16, 15, are controlled, preferably by computer means, so as to provide X- and Y-coordinate set-point demand-value control of the patient support table top. The problem of providing sets of three set-point angle values phi1, phi2 and phi3 to the required accuracy to control the associated angular displacement servos, from corresponding pairs of set-point coordinates Xa(setp), Ya(setp) provided either by manual input from an operator or in a sequence of demand values in cartesian coordinates which represent steps in a program for table top displacement during a treatment or a simulation, can be solved in various ways.

A direct X-Y to angle phi 1, 2, 3 mathematical coordinate transformation could be attempted. Such a transformation would be non-linear and could be very difficult if not impossible to formulate to the desired accuracy in a practically useful manner. Alternatively, an iterative process of numerical approximation could be attempted, but this could take too long to achieve the required accuracy for use as a real time process on a computer or microprocessor. A look-up table could be employed, however, for a positional accuracy of 0.1 mm in 1 m some 400M to 600M bytes of storage would be required. If a much coarser look up table with, for example, ten base points for each horizontal coordinate, were employed and interpolation carried out using stored base point angles and X and Y angular gradients for each angle phi1, phi2 and phi3, as little as 4K bytes of memory could be employed, but the overall accuracy of the interpolation will be very dependent on position and can become unacceptable for certain combinations of angular values.

The reverse coordinate transformation which enables the actual horizontal cartesian coordinates Xa(act), Ya(act) of the patient reference point a to be calculated from present angular values phi1(act), phi2(act) and phi3(act) measured by the data sensors 116A, 104A and 83A, is however much easier to process to the required accuracy in real time by a computer or microprocessor. A generalised form of this reverse transformation is given by equation 1, 2 and 3 on the accompanying sheet of equations. Present values Xa(act), Ya(act) computed using these equations, can be compared by a process of subtraction with momentary set-point demand values Xa(setp), Ya(setp) provided for example by a treatment program displacement sequence, to generate error (i.e. difference) values EX, EY. These difference values can be used when combined in accordance with an appropriate polarity, to provide angular error drive signals for respective open-loop angular drive servos to provide a suitable nulling servo arrangement. However, such an attempt to control two or more operationally independent but globally interrelated angular displacement variables can give rise to control and stability problems when the initial cartesian errors are too large. It is therefore desirable to provide a coarse initial positioning control arrangement based on a look-up table to bring the angular drive servos to within a few degrees of the correct position before enabling the nulling arrangement to operate.

As hereinbefore mentioned in relation to the setting-up procedure and as shown by equation 3, the motor drive 64, 65, 66 which alters phi3 is arranged as an angular-value set-point servo controlled by the difference between the angular value alpha (+360 degrees) and the sum of phi1(act) and phi2(act). By operating on the actual momentary values of phi1 and phi2, the orientation of the longitudinal axis of the patient support table is maintained constant in space for a constant value of alpha so that the patient does not suffer an undesirable yawing motion as the angles phi1 and phi2 are altered, possibly at different rates, by the nulling servo arrangement. As a further beneficial consequence, the nulling servo will only have to operate on the phi1 and phi2 drives.

Figure 9:
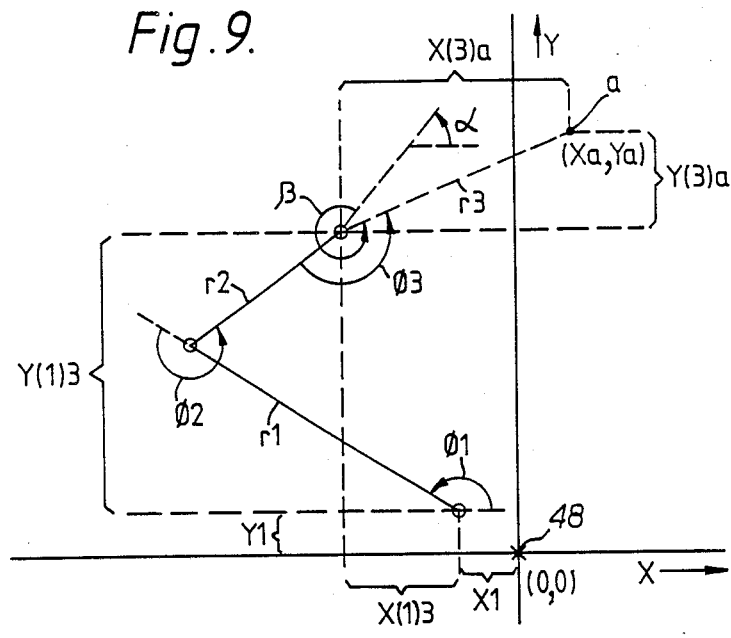
FIG. 9 is a diagram illustrating a forward transform factor field.

The transformation defined by equations 1 and 2 may be further simplified by noting that the coordinates X1, Y1 are fixed relative to the origin X0, Y0, and for a given treatment or simulation, the last term containing r3 which represents a further offset of X3, Y3 from Xa, Ya, will only vary if the angle alpha is varied since r3 and beta are measured during the setting up procedure and remain constant during a treatment or simulation run. This is indicated by equations 4 and 5. This means that the first and last terms X1, Y1 and X(3)a, Y(3)a can be regarded as constant offsets (unless alpha varies in the latter case) for the purpose of processing the transformation data. Thus the reverse transformation can be simplified as illustrated by equations 6 and 7 to which these constants can be added as in equations 8 and 9, so that only the drives which control phi1 and phi2 require to be included in the nulling servo arrangement. FIG. 9 illustrates the displacements.

One form of coordinated control arrangement for a three-axis patient support system which forms the subject matter of our co-pending U.K. Patent Application No. (PHQ87004) is illustrated diagrammatically in FIG. 10 (which is partly a flow diagram for the processing of data) in which most of the blocks represent arithmetical operations which can be carried out digitally by a computer or microprocessor in a programmed sequence related to a data sampling cycle controlling the aquisition of angular position data and programmed set-point demand values. Alternatively some or all of the blocks can be implemented by corresponding hardware elements.

The angular displacements phi1, phi2 and phi3 are effected by servo systems represented by blocks 131, 132 and 133 respectively. Each servo system includes the corresponding velocity sensor which provides a velocity feedback loop to supply damping. This is preferably performed using analogue signals to provide a smooth control undisturbed by the sampling effects of a digital system. A further velocity signal can be provided as a feed forward signal by the coordinated control system, in order to overcome steady state velocity errors, if desired. The servos 131 and 132 are arranged in a final nulling process of error reduction, as open loop servos, and are controlled by a corresponding input error (drive) signal Ephi1 an Ephi2 via a respective digital-to-analog converter 134, 135. The derivation of these drive signals in the overall nulling system and coarse error-reduction system, will be described later. The servo 133 is a set-point servo which is arranged to make phi3(act) measured by the data sensor 83A, equal to the difference between alpha and the sum of phi1(act) and phi2(act) obtained by a computing process indicated by the block 136. The result from 136 is applied with the output from 83A to a differencing process 137 to detect any error Ephi3 in accordance with equation 17 in which the measured actual values are employed. The actual values and the processes 136 and 137 are preferably carried out digitally to a sufficient degree of accuracy, and the error signal Ephi3 is then converted by a digital-to-analog converter 138 to provide the analog error drive signal for the servo 133. The momentary value representing the angle alpha, block 139, is stored at an available location in memory and may be a value provided by the operator at the start of an operation, or may be the present value from a sequence of values forming part of a treatment or simulation control program. The general control and operating system is indicated by the block 140, and a manual input keyboard 141 is provided. The system 140 can comprise a small general purpose computer or can be made up of one or more microprocessor based systems.

The dashed line boundary 142 indicates the processes involved in the nulling servo arrangement, by means of which set-point coordinate values Xa(setp) and Ya(setp) demanded via the control system 140 by the operator or by a treatment or simulation program, are converted into corresponding angular positions phi1 and phi2 by the open loop servos 131 and 132.

A main computing process in this conversion is the reverse transformation calculation represented by the block 143. The actual values phi1(act) and phi2(act) are sampled from the position sensors 116A and 104A and are applied to 143 where these values are used as indicated by equations 6 and 7 to generate actual values X(1)3(act) and Y(1)3(act). The constant values X1, Y1 relating to the origin offset (if any), and the quasi constant offset X(3)a, Y(3)a of the point a from the third axis X3, Y3 which will have been determined optically at the start and will be modified whenever the demand value of alpha (block 139) is changed, are supplied from corresponding memory locations 144 and 145, respectively. These offsets are added to the generated values X(1)3(act), Y(1)3(act) in accordance with equations 8 and 9 to provide actual coordinate values Xa(act) and Ya(act), relating to the patient reference point a. These operations are illustrated by FIG. 9.

The respective actual values Xa(act), Ya(act) are subtracted from the corresponding set-point demand values Xa(setp) and Ya(setp) provided by the control system 140, by a differencing process indicated by 146 and 147, respectively, to provide error quantities EX, EY representing the magnitude and sign of the cartesian error components. Before such error values can be applied to form a drive signal to the angular drive servos 131 and 132 the signs (polarities) of EX and EY must be related to the corresponding error (drive) signals Ephi1 and Ephi2 which would be required in each case to drive the corresponding servo 131, 132 in a direction which would tend to reduce the given error EX or EY. When the errors are not too large the appropriate polarity will be provided in each case by multiplying the cartesian error component EX, EY by the corresponding partial differential coefficient with respect to the relevant angle phi1 or phi2. These differential coefficients are given by equations 10, 11, 14 and 14 and are derived computationally as indicated by blocks 148, 149, 150 and 151. The respective subsequent multiplication steps are indicated by blocks 152, 153, 154 an 155 after which the modified error values relating to the same angle are added at 156 and 157 to provide angular error signals Ephi1 and Ephi2 as indicated by equations 15 and 16.

The differential coefficients ought strictly to relate to the coordinates and related angles represented by the set-point demand values Xa(setp), Ya(setp), however, when the servo errors are small and the system is following a series of closely adjacent values, it is sufficient to use differential coefficients calculated from the actual values of phi1 and phi2 since the relevant coefficients will tend towards the correct values as the null balance point is approached.

Calculation of the differential coefficients does not add significantly to the data processing time since the values of the sine and cosine terms will already have been derived for the basic transformation equations 8 and 9 and can be stored for subsequent use in equations 10, 11, 13 and 14. The additions required by equations 10 and 11 must be carried out to the full digital accuracy because for some combinations of angles the result will give small near-zero values from the difference of two relatively large values, and it is important for the value of the coefficient to pass through zero and to reverse in sign at the correct angular values to avoid an unnecessary amount of drive being applied to a rotation servo by a significant cartesian error signal relating to a coordinate which happens at that moment to be directed at right angles to, i.e. in quadrature with, that rotation. It is not however important that the absolute value of the resultant differential coefficient be followed exactly above about ten percent of the maximum amplitude, consequently a process of amplitude limitation can be applied enabling multiplication to take place using a smaller number of digits hence saving computing time.

Although the nulling servo arrangement described so far can function correctly when the set-point demand values applied are relatively close to the actual position values, difficulties arise when a large difference in position values is presented, for example as the result of a manual input command or an initial step or a large change in a treatment pattern. Thus it will be apparent from equations 15 and 16 that situations could occur where the EX and EY terms may be equal but opposite in sign giving rise to a zero angular drive in one of the servos while the errors are still large. In most cases this will only occur in one of the servo channels, and continued operation of the other servo would soon remove the balancing equality. There may also be instances when the resultant drive will tend to cause an angular displacement servo to start to move in the wrong direction as a result of calculating the differential coefficient from the actual angles and may even cause the drive to lock-up against an end stop in the case of phi1. Thus, because of the non-linear relationship between the cartesian coordinate values and the angles phi1 and phi2 it is desirable to provide a coarse angle control arrangement indicated by the dashed outline 160 which includes a coarse look-up table represented by the block 161, and which provides substitute drive signals to the servos 131 and 132 whenever either or both actual cartesian coordinate value, e.g. Xa(act), Ya(act), departs by more than a predetermined amount from the set-point demand values.

The look-up table 161 comprises a two-dimensionally organised storage facility, suitably implemented by a ROM or an EPROM matrix store, and can be addressed in accordance with the more significant digits representing the quantities X(1)3(setp) and Y(1)3(setp) derived from the values Xa(setp), Ya(setp) by subtracting the origin offset X1, Y1 and the patient reference point offset X(3)a, Y(3)a as indicated by blocks 162, 163. The addressed store 161 then outputs respective coarse values phi1c and phi2c which have been computed and adjusted on manufacture to provide initial demand angle settings for the servos 131 and 132 to aim for. The coarse values phi1C and phi2C are applied to respective differencing processes 164, 165 together with the actual values phi1(act), phi2(act) from the position sensors 116A, 104A so as to provide initial angular error (drive) signals Ephi1c, Ephi2c. The cartesian error signals EX, EY are applied to a comparison process 166 in which the absolute values of EX and EY are compared with a predetermined value k and when either or both exceed that value both switch processes 167 and 168 are changed over so that the error drive signals input to the servos 131 and 132 via the D/A converters 134, 135, are provided by the signals Ephi1c and Ephi2c formed from the coarse values generated by the look-up table 161. Once the servos 131, 132 have in this way been driven to the point at which EX, EY are both less than k, both the switches 167 and 168 revert to the original state and the nulling servo 142 operates as hereinbefore described.

The field of X(1)3, Y(1)3 values represented by the table 161 must, of course be more extensive than the required displacement field for the patient reference point a about the isocentre, and which could for example be about 1 m square, because allowance must be made for the range of variation to be expected in the patient reference point offset X(3)a, Y(3)a, and this might further amount to about 1 m square. Thus the maximum field required for the distances X(1)3, Y(1)3 represented in the look-up table 161 would be about 2 m square and both dimensions can each be satisfactorily divided into fifteen equal intervals giving a grid of 256 spot values. If the corresponding angles phi1 and phi2 are each coarsely represented by one byte (eight bits) at the related addresses, only about 1K of storage will be required, and the angles can be represented to within about 1.5 degrees.

The value of k employed in the comparison process 166 must be selected so as to ensure that for all the stored pairs of spot values of phi1 and phi2 in the look-up table, both EX and EY will fall below the value k well before both the servos 131 and 132 reach the stored demand values of phi1 and phi2 from any direction in the X(1)3, Y(1)3 field. Thus the value of k could be set at about ten percent of the maximum possible value representing X(1)3 or Y(1)3, and such a value should enable the nulling servo arrangement 142 to complete the positioning process without difficulty.

Figure 10:
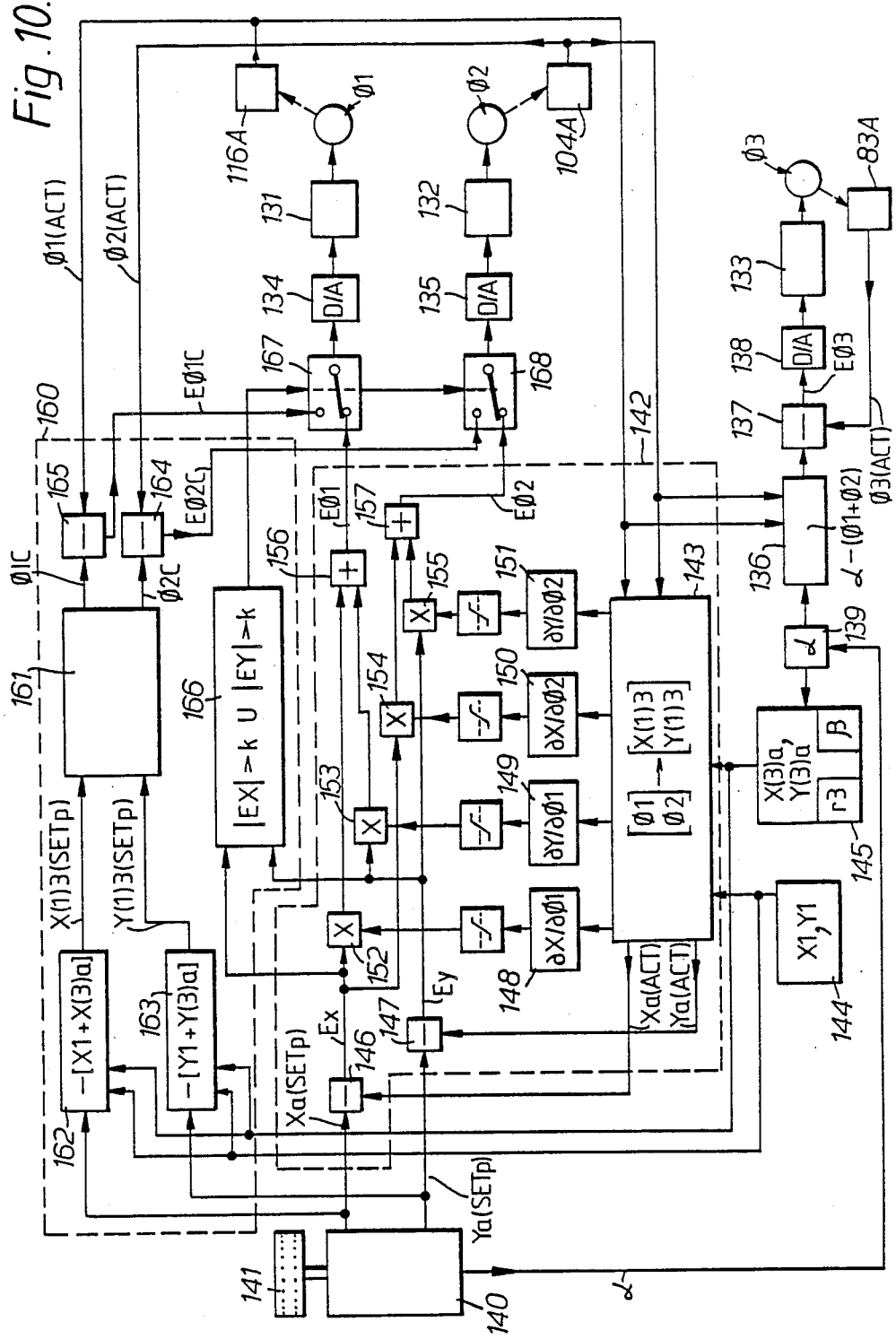
FIG. 10 is a block diagram illustrating a control arrangement for the patient support system shown in FIG. 1.

Modifications and alternatives to the control arrangement illustrated and described with reference to FIG. 10, can be employed. Thus, in determining the appropriate polarities for the cartesian error components EX and EY which are to be combined to form the angular error (drive) signals Ephi1 and Ephi2, the partial differential coefficients generated from the actual values of the angular positions phi1 and phi2, can be replaced by data relating to the appropriate polarities which is stored in a look-up table organised in a similar manner to the table 161. For example, the quantities X(1)3(setp) and Y(1)3(setp) can be employed to address a stored set of polarity coefficients, e.g. −1, 0, +1, relating to EX and EY, and to Ephi1 and Ephi2 near the corresponding null point of balance at the demand values X(1)3(setp) and Y(1)3(setp). The coefficient zero may be required when a respective quadrature control condition for either EX or EY lies within the expected balancing range. Preferably such a look-up table would also $tore coarse demand values for phi1 and phi2 as in the case of table 161, for use in a similar manner when either or both cartesian error values are large.

What is claimed is:

1. A patient support system for positioning a patient relative to an irradiation therapy or treatment simulation isocentre fixedly positioned relative to a treatment room floor comprising:

a structural support fixedly positioned with respect to said floor; a generally horizontally extended main supporting arm rotationally attached at one end to said structural support by a first support bearing, said first support bearing defining a first vertical axis about which said main supporting arm is rotatable;

a further generally horizontally extended supporting arm rotationally attached at one end to the other end of said main supporting arm by a second support bearing, said second support bearing defining a second vertical axis about which said further support arm is rotatable;

vertical support means rotationally attached to the other end of the further supporting arm by a third support bearing, said third support bearing defining a third vertical axis about which said vertical support means is rotatable;

supporting carrier means carried by said vertical support means for selective vertical displacement; and first, second and third motor drives operatively coupled respectively with said first, second and third support bearings for respectively selectively rotating said patient support top about said first, second and third axes.

2. A patient support system as claimed in claim 1 characterized in that the vertical support means comprises a single vertical supporting pillar of rigid closed box construction, an angled open V-shaped transverse section fixedly carried by the pillar, and in that the supporting carrier means comprises a vertically displaceable carriage of rigid box construction and further comprising means for locating and vertically displacing the supporting carrier means which includes two longitudinal guide tracks which are rigidly mounted adjacent one another at a mutual angle with respect to one another on the angled open V-shaped transverse section, the vertically displaceable carriage being provided with bearing members which engage the longitudinal guide tracks so as to locate and support the carriage in a vertically displaceable manner relative to the pillar, the mutual angle between the guide tracks being such that, in cooperation with the bearing members, the carriage is retained and located horizontally relative to the pillar.

3. A patient support system as claimed in claim 2, characterized in that the mutual angle between the the guide tracks is a right angle.

4. A patient support system as claimed in claim 2, characterized in that the open V-shaped transverse section is formed by an outer wall surface of the vertical supporting pillar.

5. A patient support system as claimed in claim 2, characterized in that the means for locating and vertically displacing the supporting carrier means include a motor driven rotatable screw threaded shaft mounted in a thrust bearing supported by the vertical supporting pillar, said shaft engaging a corresponding nut attached to the vertically displaceable carriage.

6. A patient support system as claimed in claim 1, characterized in that the main supporting arm is located below the floor of the treatment room, the further support arm is located above the floor, and an arcuate angularly directed aperture is provided in the surface of the floor along the path of the other end of said main support arm when said main support are is rotated about said first axis, and further comprising connecting means passing through said aperture connecting said other end of the main supporting arm to said one end of the further supporting arm via the second support bearing, the arcuate aperture being covered by a flexible cover strip, there being an angularly directed passageway formed in the connection means through which the flexible cover strip is passed.

7. A patient support system as claimed in claim 6, characterized in that the flexible cover strip comprises a plurality of angularly spaced load-bearing segments flexibly linked to one another, said arcuate aperture having sides provided with a supporting ledge means for supporting said segments so that an upper surface of the flexible cover strip formed by said segments is flush with the surface of the floor.

8. A patient support system as claimed in claim 6, characterized in that the passageway formed in the connecting means includes a smooth-walled duct to guide the flexible strip past supporting interconnections forming part of the connecting means.

9. A patient support system as claimed in claim 8, characterized in that bearing rollers are arranged along the path of the flexible strip through the passageway formed in the connecting means so as to guide the flexible strip past supporting interconnections forming part of the connecting means.

10. A patient support system as claimed in claim 1, characterized in that the main supporting arm comprises a first arm portion attached to the first support bearing and supporting a turntable surface level with the surface of the floor, and a further arm portion extending outwardly above the floor level from the outer part of the turntable surface, the second support bearing being attached to the outer end of the further arm portion.

11. A patient support system as claimed in claim 1, further comprising output shaft angular position and velocity sensing means mounted for sensing rotation about said first, second and third axes and control means for controlling the motor drives in response to the outputs of the respective sensing means and in response to a desired position of said patient support top.

12. A patient support system as claimed in claim 11, characterized in that the motor drives are provided with electric drive motors.

13. A patient support system as claimed in claim 12, characterized in that at least one of the electric motor drives includes reduction gearing employing a harmonic drive arrangement.

14. A patient support system as claimed in claim 13, characterized in that the harmonic drive is a strain wave gear arrangement employing a two lobed strain inducing element.

* * * * *